(12) United States Patent
Kanegasaki et al.

(10) Patent No.: US 8,568,660 B2
(45) Date of Patent: Oct. 29, 2013

(54) DISK, AND COUNTING OBSERVATION APPARATUS FOR COUNTING AND OBSERVING CELLS THROUGH OPTICAL MICROSCOPE BY USE OF THE DISK

(75) Inventors: Shiro Kanegasaki, Tokyo (JP); Takafumi Iseri, Tokyo (JP)

(73) Assignee: Hirata Corporation, Tokyo (JP)

( * ) Notice: Subject to any disclaimer, the term of this patent is extended or adjusted under 35 U.S.C. 154(b) by 1566 days.

(21) Appl. No.: 11/448,878

(22) Filed: Jun. 8, 2006

(65) Prior Publication Data

US 2007/0063142 A1      Mar. 22, 2007

(30) Foreign Application Priority Data

Sep. 16, 2005  (JP) ................. 2005-269818

(51) Int. Cl.
*G01N 21/00*      (2006.01)
(52) U.S. Cl.
USPC ........................................ 422/82.05
(58) Field of Classification Search
USPC ........................................ 422/82.05
See application file for complete search history.

(56) References Cited

U.S. PATENT DOCUMENTS

| | | | |
|---|---|---|---|
| 5,478,527 A * | 12/1995 | Gustafson et al. | 422/82.11 |
| 5,545,438 A | 8/1996 | Ouyang et al. | 427/299 |
| 2002/0118355 A1* | 8/2002 | Worthington et al. | 356/72 |
| 2003/0133840 A1* | 7/2003 | Coombs et al. | 422/82.05 |
| 2003/0219713 A1* | 11/2003 | Valencia et al. | 435/4 |
| 2005/0037484 A1 | 2/2005 | Staimer et al. | 435/287.2 |

FOREIGN PATENT DOCUMENTS

| | | |
|---|---|---|
| JP | 08082590 A | 3/1996 |
| JP | 3434064 | 5/2003 |
| JP | 2004-348104 | 12/2004 |
| WO | WO 2004095034 A1 * | 11/2004 |

OTHER PUBLICATIONS

Draft of amendment for instant claim sent by Applicant's representative. Jun. 12, 2009.*
"Silicon Dioxide," Wikipedia website, Sep. 11, 2009.*
Lenntech Water Treatment website, 1998-2009, p. 1-2, <http://www.lenntech.com/periodic/water/aluminium/aluminum-and-water.htm>.*
Lenntech Aluminum (Al) and water, Jun. 16, 2009, http://www.lenntech.com/elements-and-water/aluminum-and-water.htm.

* cited by examiner

*Primary Examiner* — Bobby Ramdhanie
*Assistant Examiner* — Bryan Kilpatrick
(74) *Attorney, Agent, or Firm* — Bacon & Thomas PLLC

(57) ABSTRACT

A disk for storing liquid samples containing cells and for use in counting and observing the cells through an optical microscope includes an upper member formed of a transparent material and having a plurality of liquid inlets arranged radially and adapted to introduce the corresponding liquid samples therethrough, and a plurality of air vents paired with the corresponding liquid inlets; an intermediate member having a plurality of chambers arranged radially and adapted to store the corresponding liquid samples therein, each chamber corresponding to each pair of the liquid inlet and the air vent and communicating with the liquid inlet and with the air vent; and a lower member formed of a transparent material and backing the intermediate member. The optical microscope assumes the form of an incident-light microscope.

11 Claims, 17 Drawing Sheets

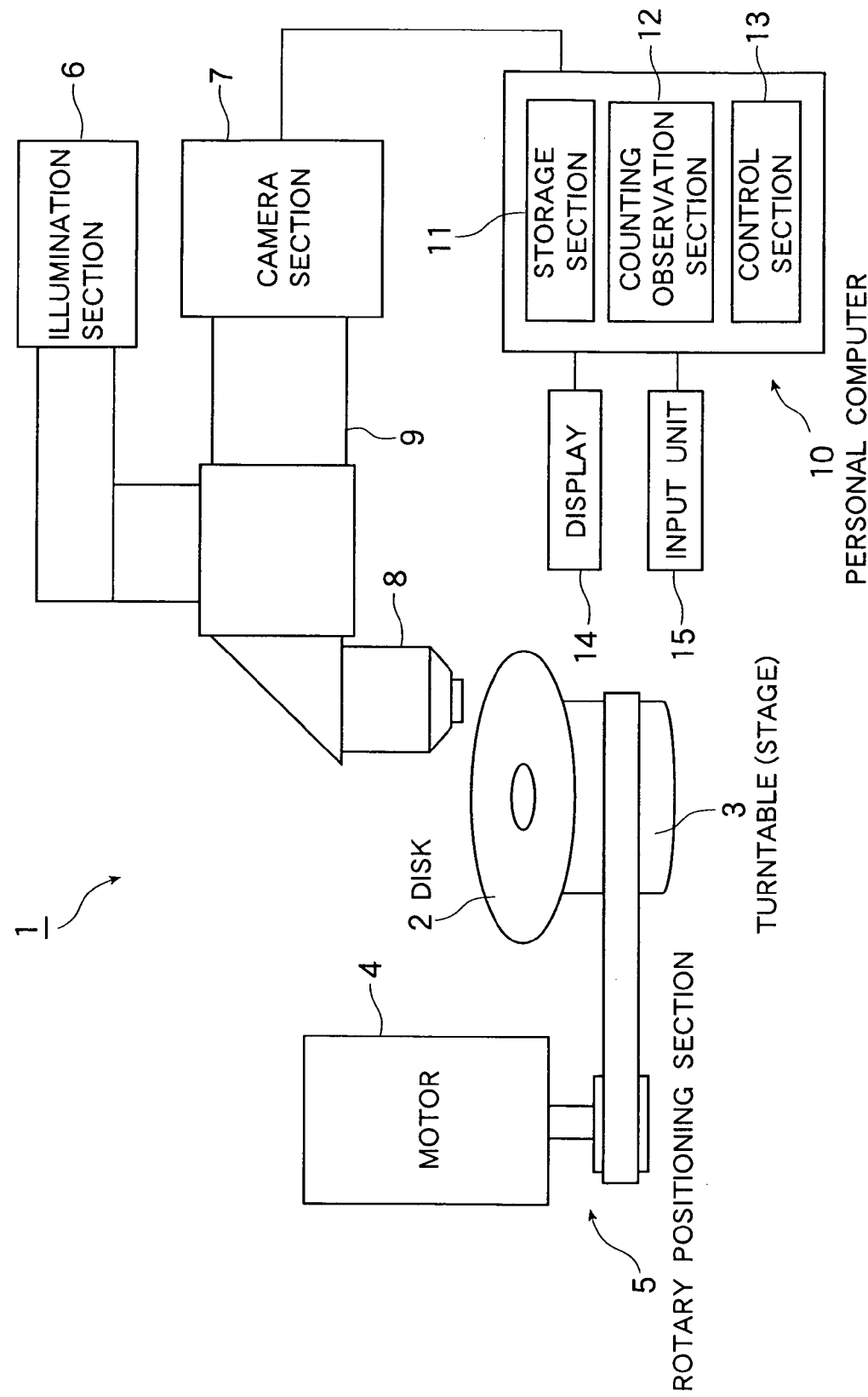

Fig.9
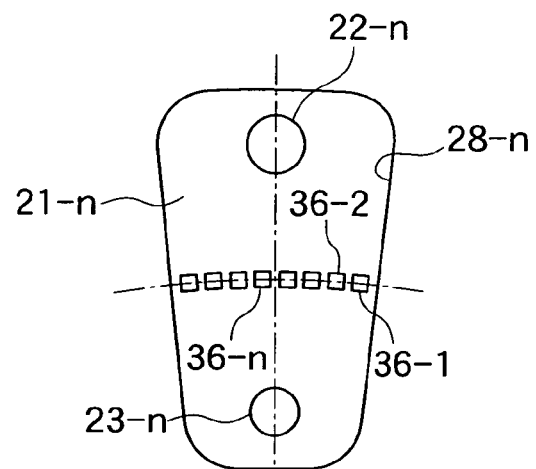
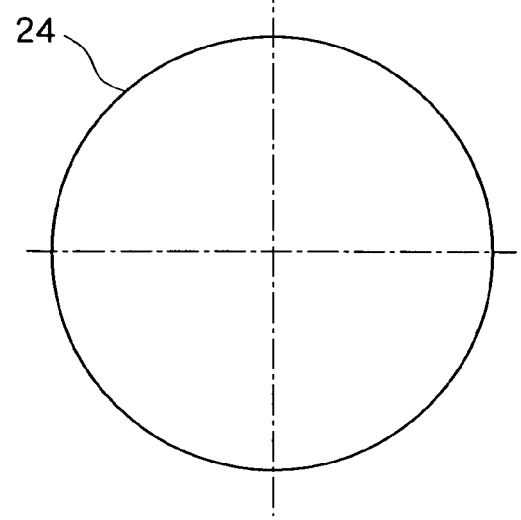

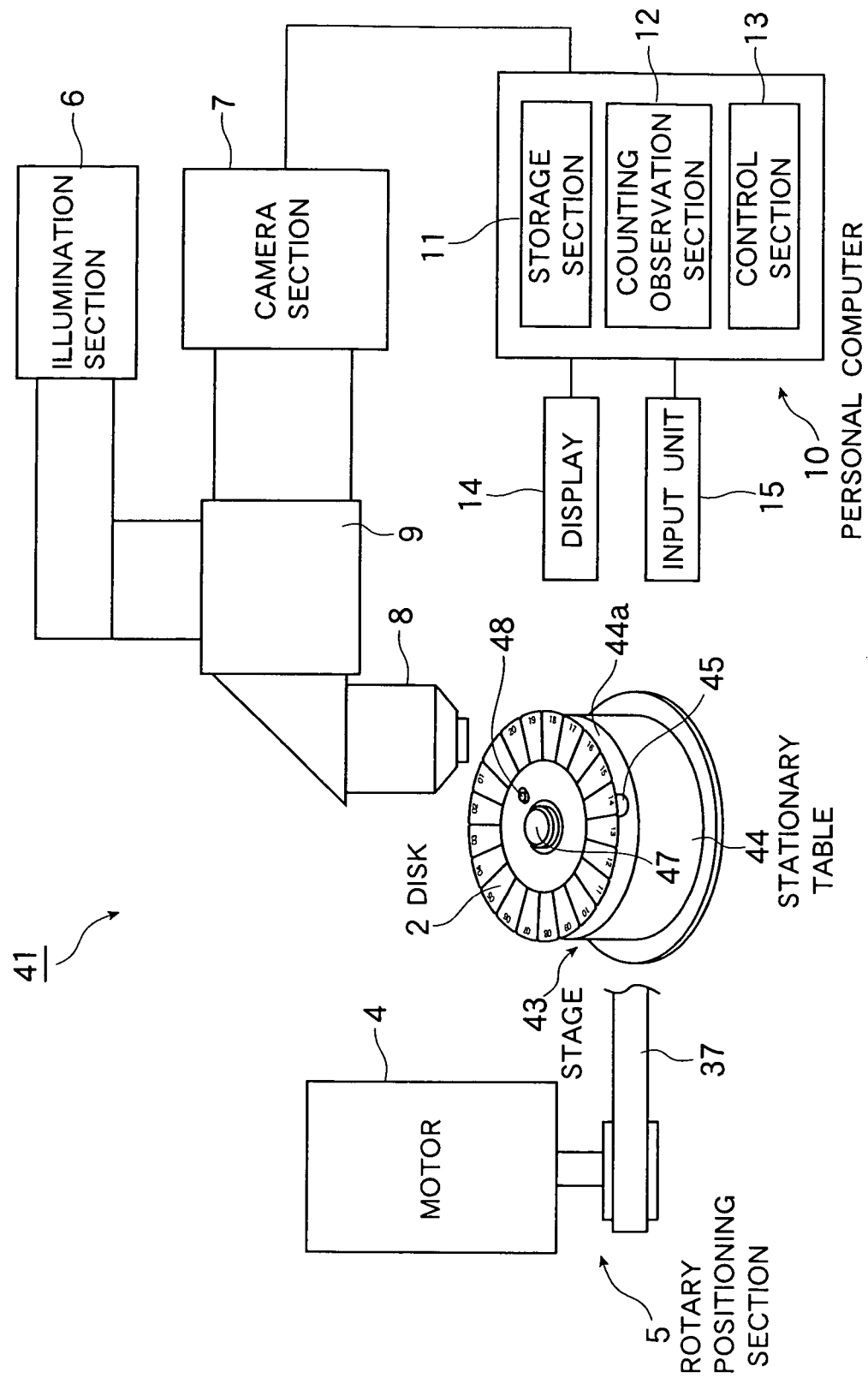

DISK, AND COUNTING OBSERVATION APPARATUS FOR COUNTING AND OBSERVING CELLS THROUGH OPTICAL MICROSCOPE BY USE OF THE DISK

BACKGROUND OF THE INVENTION

1. Field of the Invention

The present invention relates to a disk for storing liquid samples and used to count and observe cells in the liquid samples, as well as to a counting observation apparatus for counting and observing cells through an optical microscope by use of the disk. More particularly, the present invention relates to a disk for storing liquid samples used to count and observe cells in the liquid samples which can be readily fabricated at low cost, as well as to a counting observation apparatus for counting and observing cells through an optical microscope by use of the disk which can be fabricated in a reduced size and at low cost.

2. Description of the Related Art

Many conventional disks for storing liquid samples and used to count and observe cells in the liquid samples are configured such that a cover member covers, from above, a lower structure in which a plurality of accommodation recesses for storing respective liquid samples are arranged radially (refer to, for example, Japanese Patent Application Laid-Open (kokai) No. 8-082590 and Japanese Patent No. 2731423). In this case, the lower structure and the cover member are fabricated from transparent glass or resin material. While the disk is rotated intermittently, counting and observing cells in the liquid samples stored in the accommodation recesses are performed sample by sample through a transmission microscope.

The lower structure having the plurality of liquid-sample accommodation recesses is fabricated from transparent glass or resin material by means of a forming process. Thus, finishing the liquid-sample accommodation recesses at dimensionally high accuracy is not easy. Since an illumination light source and an optical system oppose each other with a liquid sample located therebetween, the counting observation apparatus using the transmission microscope has a drawback that its size becomes large.

In order to avoid an increase in the size of a counting observation apparatus, there have been proposed counting observation apparatus for counting and observing cells by use of an incident-light microscope in which an illumination light source and an optical system are disposed on the same side in relation to a liquid sample, while a reflector is disposed behind the liquid sample (refer to, for example, Japanese Patent No. 3434064 and Japanese Patent Application Laid-Open (kokai) No. 2004-348104). However, the apparatus disclosed in Japanese Patent Application Laid-Open (kokai) No. 2004-348104 uses a nonrotatable, rectangular-parallelepiped-shaped container for storing a liquid sample, and the apparatus disclosed in Japanese Patent No. 3434064 does not mention a container for storing a liquid sample.

SUMMARY OF THE INVENTION

An object of the present invention is to solve the above-mentioned problems in the conventional disk for storing liquid samples and in the conventional counting observation apparatus for counting and observing cells by use of an optical microscope, and to provide a disk for storing liquid samples which can be readily fabricated at low cost with high dimensional accuracy, as well as a counting observation apparatus for counting and observing cells through an optical microscope by use of the disk which can be fabricated in a reduced size and at low cost.

To achieve the above object, the present invention provides a disk for storing liquid samples containing cells and for use in counting and observing the cells through an optical microscope, comprising an upper member formed of a transparent material and having a plurality of liquid inlets arranged radially and adapted to introduce the corresponding liquid samples therethrough, and a plurality of air vents paired with the corresponding liquid inlets; an intermediate member having a plurality of chambers arranged radially and adapted to store the corresponding liquid samples therein, each chamber corresponding to each pair of the liquid inlet and the air vent and communicating with the liquid inlet and with the air vent; and a lower member formed of a transparent material and backing the intermediate member.

Since the disk of the present invention is configured as described above; i.e., the disk is a 3-layer laminate consisting of the upper member, the intermediate member, and the lower member, the disk can be readily fabricated. Since the dimensions of a liquid-sample accommodation portion are determined from the dimensions of each of the chambers arranged radially for storing the corresponding liquid samples, the dimensions of the liquid-sample accommodation portion; particularly, a depth, can be readily finished at high accuracy. Thus, a highly accurate disk can be readily fabricated at low cost.

Preferably, the disk of the present invention is fabricated from a disposable material.

Use of a disposable material can greatly improve efficiency in counting and observing cells.

Preferably, in the disk of the present invention, the upper member, the intermediate member, and the lower member are formed by blanking.

Employment of blanking can facilitate the low-cost fabrication of a highly accurate disk.

Preferably, in the disk of the present invention, the upper member, the intermediate member, and the lower member are bonded together by use of an adhesive.

Employment of bonding by use of an adhesive can facilitate the low-cost fabrication of a highly accurate disk.

Preferably, in the disk of the present invention, the intermediate member is a film having a uniform thickness and having an adhesive on opposite sides thereof; and the upper member, the intermediate member, and the lower member are bonded together by means of the adhesive on the opposite sides of the film.

Employment of the double-sided adhesive film can facilitate the low-cost fabrication of a highly accurate disk.

Preferably, in the disk of the present invention, a surface of the lower member on a side toward the upper member, or a surface of the lower member on a side opposite the upper member is a reflective surface.

In the case where the disk is used in a counting observation apparatus for counting and observing cells through an incident-light microscope, the reflective surface can be used to reflect illumination light. Therefore, the configuration of the incident-light microscope becomes simple.

Preferably, in the disk of the present invention, the reflective surface is formed of a metal vapor deposition film of aluminum or silver.

Employment of the metal vapor deposition film can facilitate use, as a reflective surface, of a surface of the lower member on a side toward the upper member, or a surface of the lower member on a side opposite the upper member.

Preferably, in the disk of the present invention, a hydrophilic film is vapor-deposited on one or both of mutually opposing surfaces of the upper member and the lower member.

Employment of the hydrophilic film enables uniform distribution of a liquid sample introduced through the liquid inlet of the upper member, within a liquid-sample accommodation portion (the liquid-sample accommodation portion is formed by sealing in the chamber of the intermediate member between the upper member and the lower member), whereby the liquid sample can be reliably and stably stored in the liquid-sample accommodation portion.

Preferably, in the disk of the present invention, a protective film is affixed to an outer surface of the upper member in such a manner that portions of the protective film corresponding to the chambers can be peeled off individually.

In actual use of the disk, employment of the protective film enables use of only a required liquid-sample accommodation portion(s), or a required chamber(s). Specifically, a corresponding portion(s) of the protective film is peeled off from a required liquid-sample accommodation portion(s), or a required chamber(s). The exposed liquid-sample accommodation portion(s), or the exposed chamber(s), are used for counting or observing cells. The remaining liquid-sample accommodation portions, or the remaining chambers, are left covered with corresponding portions of the protective film, thereby keeping off dust for later use; otherwise, adhering dust could cause difficulty in a later process of counting and observing cells.

The present invention further provides a counting observation apparatus for counting and observing cells through an optical microscope, comprising the disk of the present invention; a stage on which the disk is placed; a rotary positioning section for rotationally positioning the disk; an illumination section for illuminating the liquid sample with light; an image-detecting section for picking up an image of the cells and outputting the image in the form of image data; a storage section for storing the image data; a counting observation section for counting and observing the cells from the image data; and a control section for controlling the counting observation apparatus. In the counting observation apparatus, the storage section, the counting observation section, and the control section are provided in a personal computer as an information processing and manipulating section. Also, the chamber is divided into a plurality of visual fields; an image of the cells in each of the visual fields is picked up; the number of the cells is counted from image data associated with the image; and cell concentration is determined from an average number of the cells.

Employment of the above configuration can provide a counting observation apparatus for counting and observing cells through an optical microscope which can automatically count and observe cells with high reliability, accuracy, and efficiency by use of a highly accurate, easy-to-fabricate, low-cost disk and which can be fabricated at low cost.

In the case where a surface of the lower member on a side toward the upper member, or a surface of the lower member on a side opposite the upper member is a reflective surface, the reflective surface can be used to reflect illumination light; i.e., the optical microscope can function as an incident-light microscope, whereby the counting observation apparatus can be reduced in size.

Preferably, in the counting observation apparatus for counting and observing cells through an optical microscope of the present invention, the stage comprises three or more support members arranged circumferentially at appropriate intervals for supporting the disk; and one of the support members is located at a position immediately under an object lens of the image-detecting section or in the vicinity of the position, to thereby maintain a constant distance therebetween.

Employment of the three or more support members allows the disk to be supported by the support members and to be rotated while sliding on supporting surfaces of the support members, thereby isolating the disk from operational instability, such as wavy rotation caused by oscillatory movement of a disk-rotating drive system. At an observation position, the disk is supported by the support member located at a position immediately under an object lens or in the vicinity of the position, whereby a constant distance is maintained between the disk and the object lens. Thus, automatic counting and observation can be performed with high accuracy.

The present invention further provides a counting observation apparatus for counting and observing cells through an optical microscope, comprising the disk of the present invention; a stage on which the disk is placed; a rotary positioning section for rotationally positioning the disk; an illumination section for illuminating the liquid sample with light; an image-detecting section for picking up an image of the cells and outputting the image in the form of image data; a storage section for storing the image data; a counting observation section for counting and observing the cells from the image data; and a control section for controlling the counting observation apparatus. In the counting observation apparatus, the storage section, the counting observation section, and the control section are provided in a personal computer as an information processing and manipulating section. Also, the chamber is divided into a plurality of visual fields; an image of the cells in each of the visual fields is picked up; the number of the cells is counted from image data associated with the image; and cell concentration is determined from an average number of the cells. Furthermore, a surface of the stage on which the disk is placed is a reflective surface.

Employment of the above configuration can provide a counting observation apparatus for counting and observing cells through an optical microscope which can automatically count and observe cells with high reliability, accuracy, and efficiency by use of a highly accurate, easy-to-fabricate, low-cost disk and which can be fabricated at low cost.

By means of using the reflective surface of the stage to reflect illumination light, the optical microscope can function as an incident-light microscope, whereby the counting observation apparatus can be reduced in size.

Preferably, in the counting observation apparatus for counting and observing cells through an optical microscope of the present invention, the stage comprises three or more support members arranged circumferentially at appropriate intervals for supporting the disk; and one of the support members is located at a position immediately under an object lens of the image-detecting section or in the vicinity of the position, to thereby maintain a constant distance therebetween.

Employment of the three or more support members allows the disk to be supported by the support members and to be rotated while sliding on supporting surfaces of the support members, thereby isolating the disk from operational instability, such as wavy rotation caused by oscillatory movement of a disk-rotating drive system. At an observation position, the disk is supported by the support member located at a position immediately under an object lens or in the vicinity of the position, whereby a constant distance is maintained between the disk and the object lens. Thus, automatic counting and observation can be performed with high accuracy.

Preferably, in the counting observation apparatus for counting and observing cells through an optical microscope of the present invention, a disk supporting surface of the support member located at the position immediately under the object lens or in the vicinity of the position is a reflective surface.

In the above configuration, since the only reflective surface is the disk supporting surface of one support member located at the position immediately under the object lens or in the vicinity of the position, cost for vapor deposition for forming the reflective surface can be reduced greatly as compared with the case where the surface of the stage on which the disk is placed is formed into a reflective surface by means of vapor deposition. Accordingly, a low-cost counting observation apparatus for counting and observing cells through an optical microscope can be provided. In the case where, in place of vapor deposition, a mirror member is attached to the support member located at the position immediately under the object lens or in the vicinity of the position, cost for vapor deposition can be eliminated, and the possibility of quality defect associated with vapor deposition can also be eliminated.

BRIEF DESCRIPTION OF THE DRAWINGS

FIG. 1 is a schematic block diagram of a counting observation apparatus for counting and observing cells through an optical microscope by use of a disk for storing liquid samples according to a first embodiment of the present invention;

FIG. 9 is a view for describing an actual procedure for counting and observing cells in a liquid sample stored in a liquid-sample accommodation portion by means of the counting observation apparatus;

FIG. 11 is a schematic block diagram of the counting observation apparatus of FIG. 10, showing a state in which a disk is placed on a stage of the apparatus.

DESCRIPTION OF THE PREFERRED EMBODIMENTS

Figure 2A:
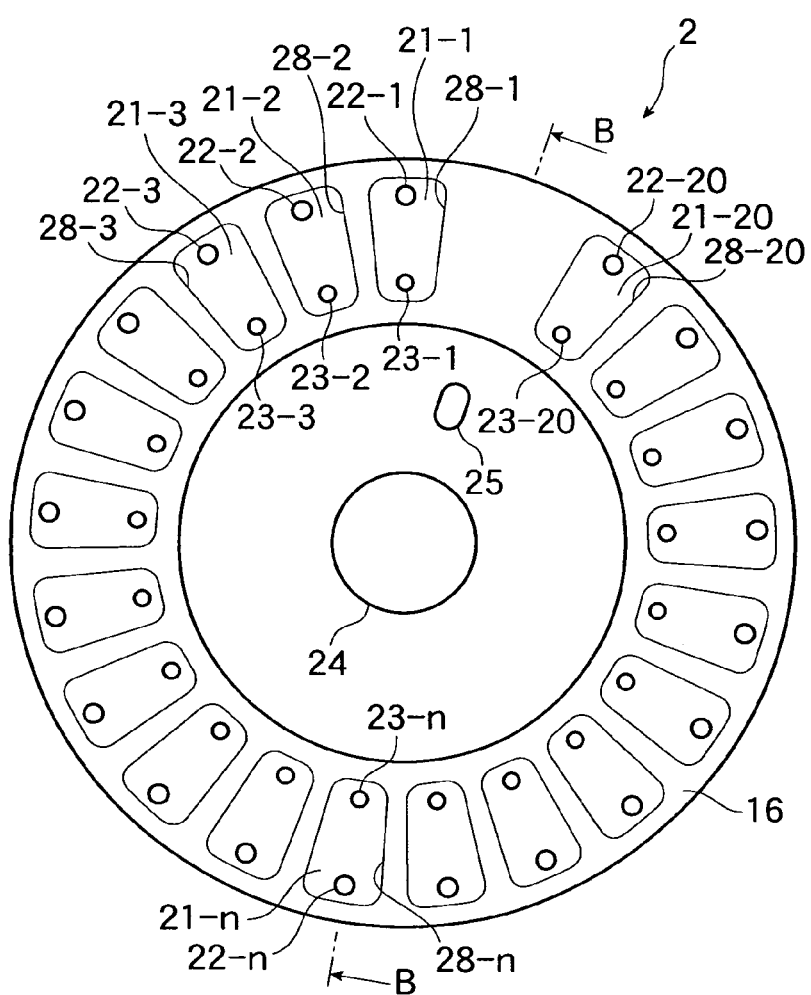
FIG. 2A is a plan view of the disk.

Embodiments of the present invention will next be described in detail with reference to the drawings.

First Embodiment

A first embodiment of the present invention will be described with reference to FIGS. 1 to 9. As shown in FIG. 1, a counting observation apparatus 1 for counting and observing cells through an optical microscope by use of a disk for storing liquid samples according to the first embodiment includes a disk 2 for storing liquid samples containing cells; a turntable 3 having a rest on which the disk 2 is placed; a rotary positioning section 5 including a motor 4 for rotationally positioning the turntable 3 and the disk 2; an illumination section 6 for illuminating the liquid sample with light; a camera section (image-detecting section) 7 for picking up (photographing) an image of cells and outputting the image in the form of image data; a storage section 11 for storing the image data; a counting observation section 12 for counting and observing the cells from the image data; and a control section 13 for controlling the counting observation apparatus. An assembly consisting of the turntable 3 and other relevant members is equivalent to a stage on which the disk 2 is placed. The storage section 11, the counting observation section 12, and the control section 13 are provided in a personal computer 10 as an information processing and manipulating section. The personal computer 10 further includes a display 14 and an input unit 15.

An optical system which includes the camera section 7, the illumination section 6, an object lens 8, and a tube section 9 serves as a microscope. Cells in a liquid sample stored in a liquid-sample accommodation portion 21-$n$, which will be described later, of the disk 2 are observed through the object lens 8 under illumination from the illumination section 6. An observed image of the cells is picked up by the camera section 7. In actuality, light led from the illumination section 6 penetrates through a liquid sample and is reflected by a reflective surface 29 provided on a lower member 17, which will be described later, of the disk 2. The reflected light passes again through the object lens 8 and is led to the camera section 7. The camera section 7 recognizes shade, resulting from reception of no light, as an image of a cell. As mentioned above, the illumination section 6 and the disk 2 are located on the same side in relation to the object lens 8; in other words, this optical microscope functions as an incident-light microscope. Accordingly, the overall height of the counting observation apparatus 1 is reduced, whereby the size of the apparatus can be reduced.

The camera section 7 picks up an image of cells, converts the image to image data, and sends (outputs) the image data to the storage section 11 of the personal computer 10. The image data which has been sent to the storage section 11 is read in real time or as needed from the storage section 11. From the read image data, the counting observation section 12 counts and observes the cells. The results of counting and observation are displayed on the display 14 and are also stored in the storage section 11.

The motor 4 of the rotary positioning section 5 is a stepping motor. The motor 4 rotates by a predetermined angle at predetermined time intervals. By this procedure, the turntable 3 is rotated by the predetermined angle to thereby rotate the disk 2 placed on the rest of the turntable 3 by the angle, whereby one of a plurality of liquid-sample accommodation portions 21-$n$ is positioned at an observation position.

While the disk 2 remains stationary for a predetermined time, the counting observation apparatus 1 counts and observes cells in a liquid sample stored in the liquid-sample accommodation portion 21-$n$ positioned at the observation position. The control section 13 of the personal computer 10 controls the rotation of the motor 4.

Next, the structure of the disk 2 will be described in detail with reference to the drawings.

Figure 2B:
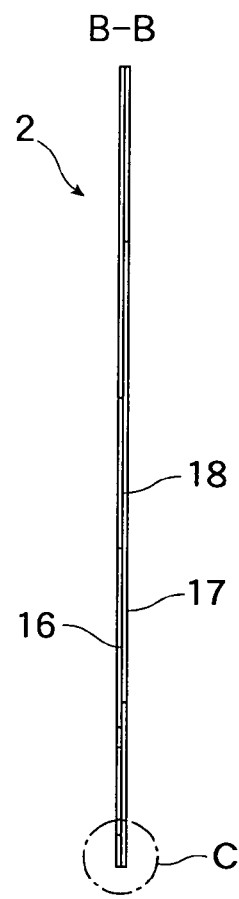
FIG. 2B is a sectional view of the disk taken along line B-B of FIG. 2A.
Figure 2C:
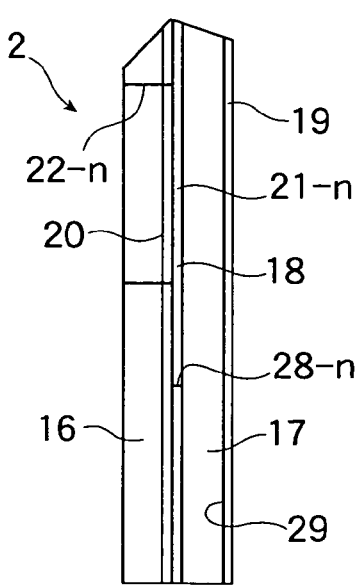
FIG. 2C is an enlarged view of region C of FIG. 2B.

For convenience of observation of cells, the counting observation apparatus 1 uses the disk 2 adapted to store liquid samples containing the cells. As shown in FIG. 2, the disk 2 assumes the form of a thin, rotary disk. A plurality of (20 in the first embodiment) the liquid-sample accommodation portions 21-$n$ (n=1 to 20) are arranged radially at circumferentially equal intervals in a radially outward, circumferential region of the disk 2. As the turntable 3, and the disk 2 placed on the rest of the turntable 3 are rotated intermittently in association with intermittent rotation of the motor 4, the 20 liquid-sample accommodation portions 21-$n$ (n=1 to 20) are sequentially brought to the observation position of the counting observation apparatus 1 through associated intermittent rotation.

The disk 2 has a basic structure of a laminate consisting of three thin plates or films; specifically, a laminate consisting of an upper member 16, an intermediate member (center film) 18, and the lower member 17.

Figure 6A:
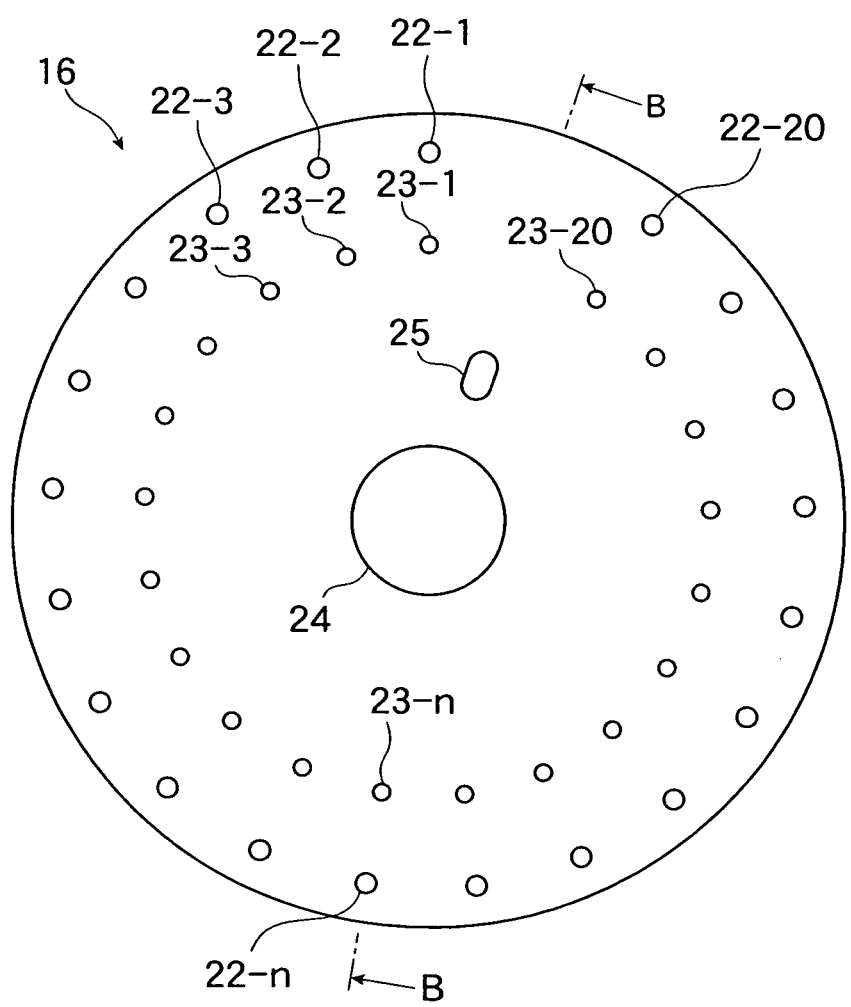
FIG. 6A is a plan view of an upper member of the disk.
Figure 6B:
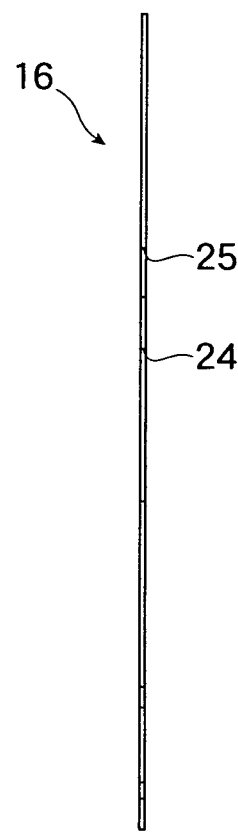
FIG. 6B is a sectional view of the upper member taken along line B-B of FIG. 6A.

The upper member 16 is formed of a transparent resin material and is located on a side toward the object lens 8 during the course of observation. As shown in FIGS. 2 and 6, the upper member 16 assumes the form of a thin disk and has a plurality of radially arranged liquid inlets 22-$n$ (n=1 to 20) through which liquid samples are introduced into the liquid-sample accommodation portions 21-$n$ (n=1 to 20), and a plurality of air vents 23-$n$ (n=1 to 20) paired with the corresponding liquid inlets 22-$n$. The air vents 23-$n$ are formed radially inward of the corresponding liquid inlets 21-$n$.

The upper member 16 also has a positioning hole 24 and a positioning hole 25. The positioning hole 24 is used to position the disk 2 which is a laminate consisting of three thin plates or films. Specifically, the positioning hole 24 is used to position the disk 2 in the X-Y direction on the rest of the turntable 3 and to perform centering for rotation of the disk 2. The positioning hole 25 assumes the form of an elongated circle as viewed in plane and is used to determine an initial angular position for rotation of the disk 2 on the rest of the turntable 3.

Figure 8A:
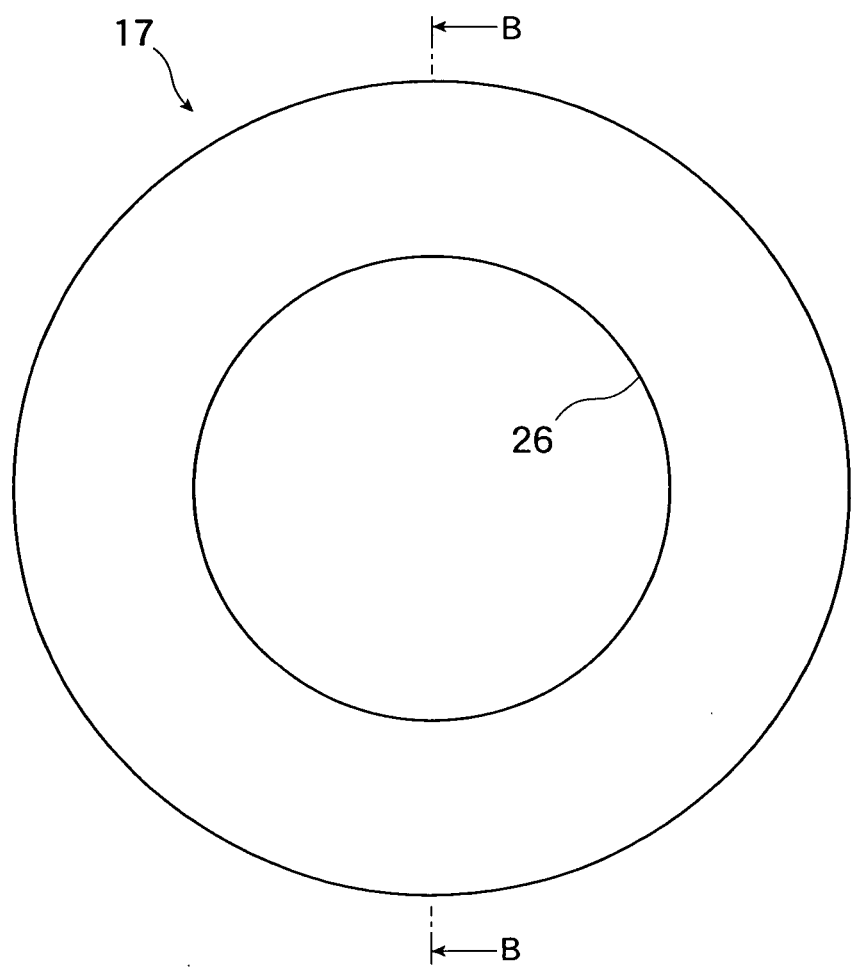
FIG. 8A is a plan view of a lower member of the disk.
Figure 8B:
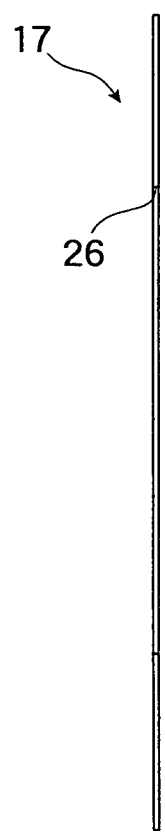
FIG. 8B is a sectional view of the lower member taken along line B-B of FIG. 8A.

The lower member 17 is also formed of a transparent resin material and is in contact with the rest of the turntable 3 during the course of observation. As shown in FIGS. 2 and 8, the lower member 17 is a thin plate having an annular shape like a doughnut as viewed in plane and has a center hole 26 of a relatively large diameter formed in a central portion thereof. The thickness of the lower member 17 is substantially equal to that of the upper member 16.

Figure 7A:
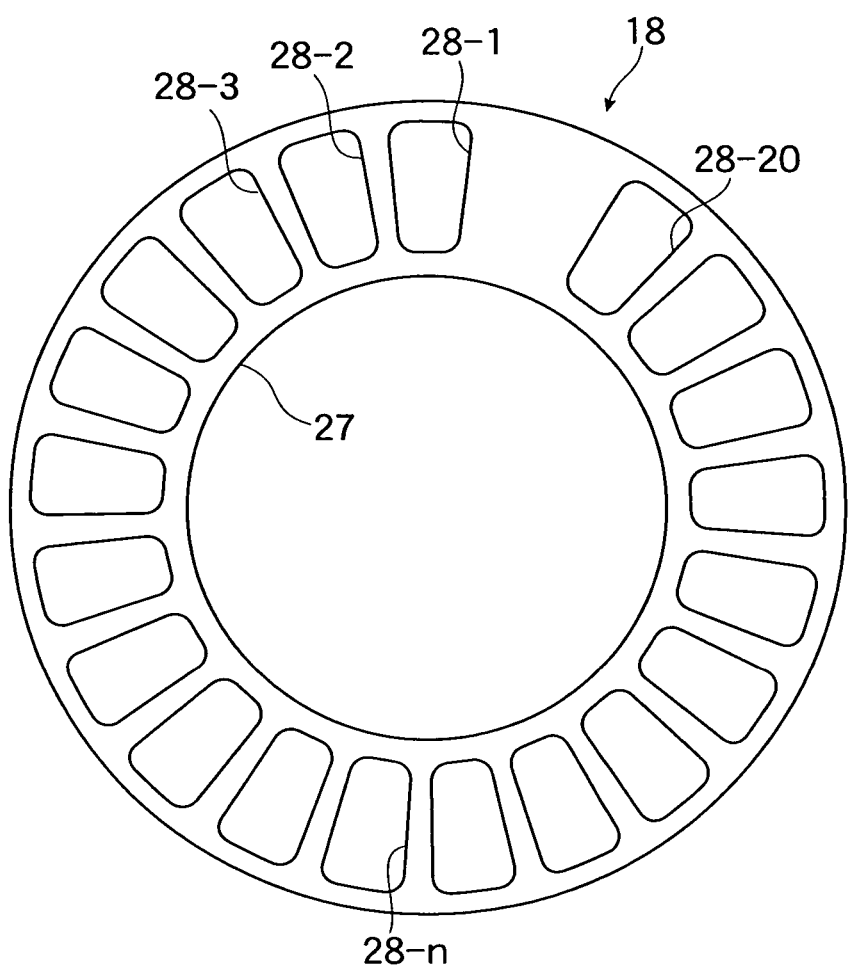
FIG. 7A is a plan view of an intermediate member (center film) of the disk.
Figure 7B:
FIG. 7B is a side view of the intermediate member.

The intermediate member (center film) 18 is also formed of a resin material, but is not necessarily transparent. As shown in FIGS. 2 and 7, as in the case of the lower member 17, the intermediate member 18 is a very thin film having an annular shape like a doughnut as viewed in plane and has a center hole 27 of a relatively large diameter formed in a central portion thereof. The diameter of the center hole 27 is substantially equal to that of the center hole 26. The thickness of the intermediate member 18 is about ⅕ that of the upper member 16 and that of the lower member 17.

A plurality of (20 in the first embodiment) chambers 28-$n$ (n=1 to 20) for storing corresponding liquid samples along the plane of the film are formed radially in the intermediate member 18 at circumferentially equal intervals to be located between the outer circumferential edge of the intermediate member 18 and the center hole 27. Each of the chambers 28-$n$ has a shape, as viewed in plane, resembling an isosceles trapezoid with four rounded corners and is oriented such that its short side is directed toward the center of the intermediate member 18.

Figure 3:
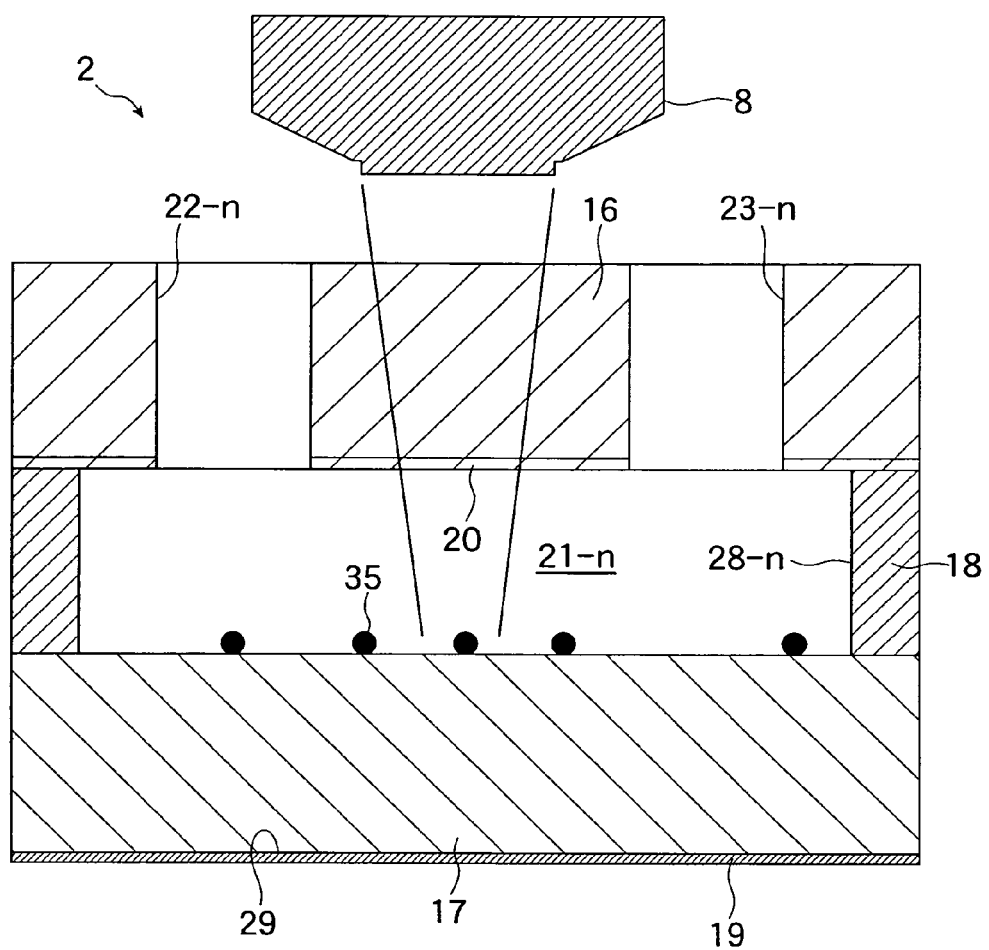
FIG. 3 is a schematic enlarged sectional view for describing a liquid-sample accommodation portion of the disk.

The intermediate member 18 is sandwiched between and bonded to the upper member 16 and the lower member 17, thereby yielding a laminate; i.e., the framework of the disk 2. As a result, the chamber 28-$n$ of the intermediate member 18 is sealed in between the upper member 16 and the lower member 17, thereby forming the liquid-sample accommodation portion 21-$n$ (n=1 to 20). The liquid-sample accommodation portion 21-$n$ is a flat closed chamber for storing and holding a liquid sample and communicates with the exterior of the disk 2 only through the liquid inlet 22-$n$ and the air vent 23-$n$ which are formed in the upper member 16. FIG. 3 shows, on an enlarged scale, the liquid-sample accommodation portion 21-$n$ and its periphery. For easy understanding, FIG. 3 is a schematic view; i.e., FIG. 3 is not a view on an accurate scale. In FIG. 3, reference numeral 35 denotes a cell.

In the disk 2, bonding between the upper member 16, the intermediate member 18, and the lower member 17 is performed actually as follows. The intermediate member 18 assumes the form of a double-sided adhesive film having an accurately uniform thickness. The adhesive on opposite sides of the film is used for bonding. As a result of the intermediate member 18 assuming the form of such a film, when the three members are bonded together to form a laminate, the liquid-sample accommodation portions 21-$n$ having high dimensional accuracy are formed in the laminate.

The upper member 16, the intermediate member 18, and the lower member 17 which are used to form the disk 2 are fabricated from respective, disposable resin materials. This greatly improves efficiency in counting and observing cells. This avoids causing pollution. Furthermore, these members are formed from the respective materials by blanking. Thus, as compared with the case where these members are fabricated by means of a forming process, these members can be fabricated far more easily.

As shown in FIGS. 2 and 3, the surface of the lower member 17 of the disk 2 which is in contact with the rest of the turntable 3; in other words, a surface of the lower member 17 on a side opposite the upper member 16, is formed into a reflective surface 29. The reflective surface 29 is obtained by forming a metal vapor deposition film 19 of aluminum, silver, or a like metal on the surface of the lower member 17 by means of sputtering or a like process. Notably, a surface of the lower member 17 on a side toward the upper member 16 may be formed into the reflective surface 29. Alternatively, the surface of the rest of the turntable 3 on which the disk 2 is placed (the surface of the rest on which the disk 2 is placed is increased in diameter such that the diameter is substantially equal to the outside diameter of the disk 2) may be formed into the reflective surface 29.

As shown in FIGS. 2 and 3, a hydrophilic film 20 is vapor-deposited on a surface of the upper member 16 of the disk 2 on a side toward the lower member 17 of the disk 2. The hydrophilic film 20 is formed by vapor-depositing silicon oxide, or $SiO_2$, on the surface of the upper member 16 by means of sputtering or a like process. Notably, the hydrophilic film 20 may be vapor-deposited on a surface of the lower member 17 on a side toward the upper member 16. Alternatively, the hydrophilic film 20 may be vapor-deposited on both of the mutually opposing surfaces of the upper member 16 and the lower member 17. The hydrophilic film 20 allows a liquid sample introduced through the liquid inlet 22-*n* of the upper member 16 to be uniformly distributed against surface tension within the liquid-sample accommodation portion 21-*n*, whereby the liquid sample can be reliably and stably stored in the liquid-sample accommodation portion 21-*n*.

Figure 4A:
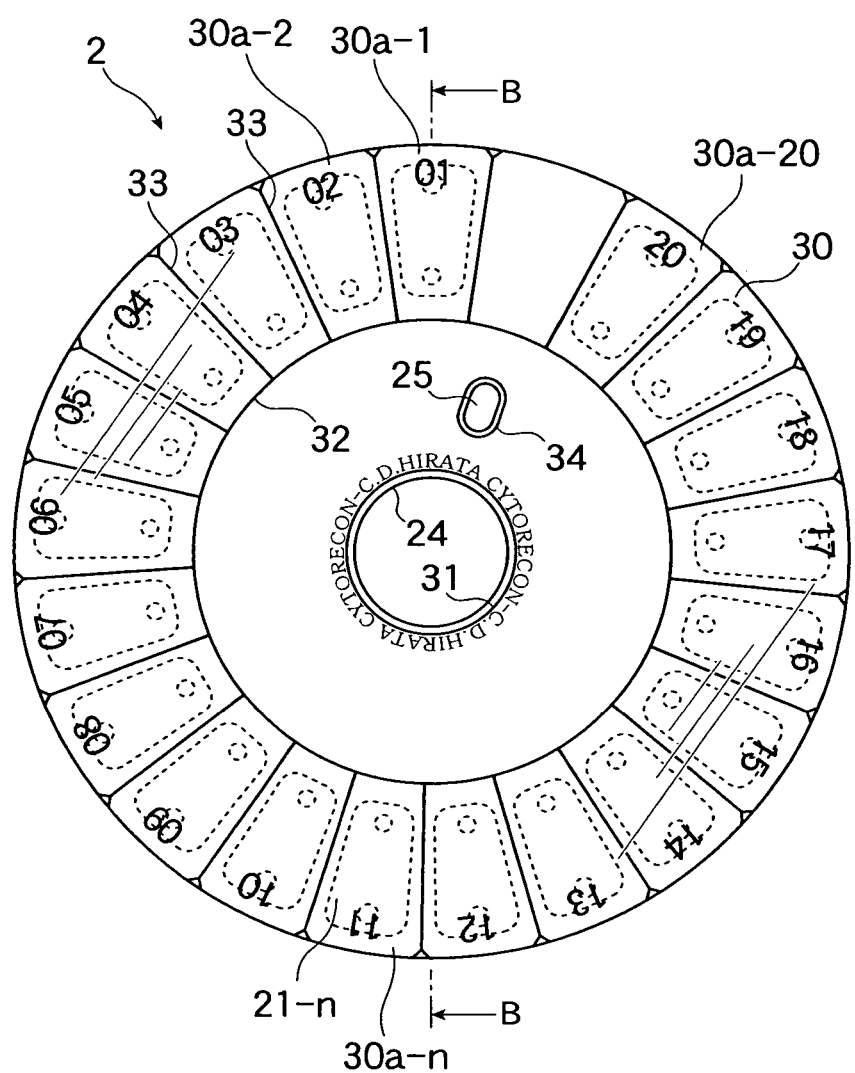
FIG. 4A is a plan view of the disk with a protective film attached thereto.
Figure 4B:
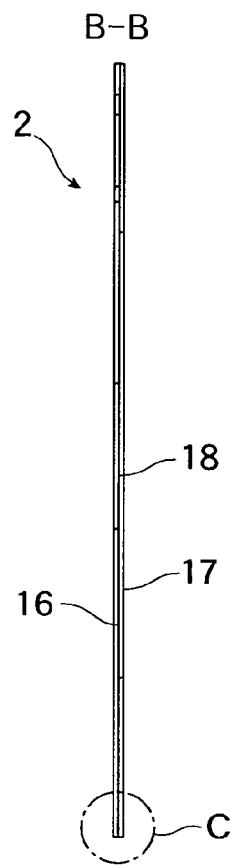
FIG. 4B is a sectional view of the disk taken along line B-B of FIG. 4A.
Figure 4C:
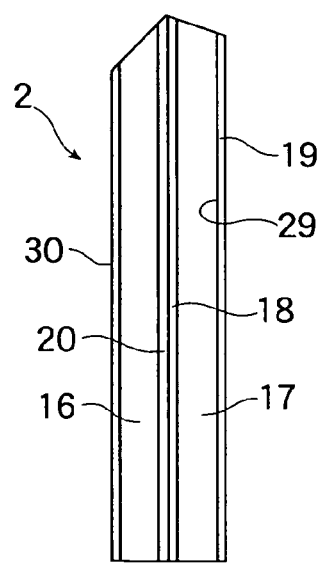
FIG. 4C is an enlarged view of region C of FIG. 4B.

As shown in FIG. 4, a protective film 30 is affixed to the outer surface of the upper member 16 of the disk 2. The protective film 30 is divided into a plurality of protective-film pieces 30*a-n* (n=1 to 20) which correspond to the individual chambers 28-*n* (n=1 to 20) of the intermediate member 18; in other words, the individual liquid-sample accommodation portions 21-*n* (n=1 to 20). The individual protective-film pieces 30*a-n* can be peeled off along their arcs 32 and line segments 33. In actual use of the disk 2, only the protective-film piece(s) 30*a-n* corresponding to the liquid-sample accommodation portion(s) 21-*n* to be used is peeled off. The exposed liquid-sample accommodation portion(s) 21-*n* can be used for counting and observing cells.

Figure 5A:
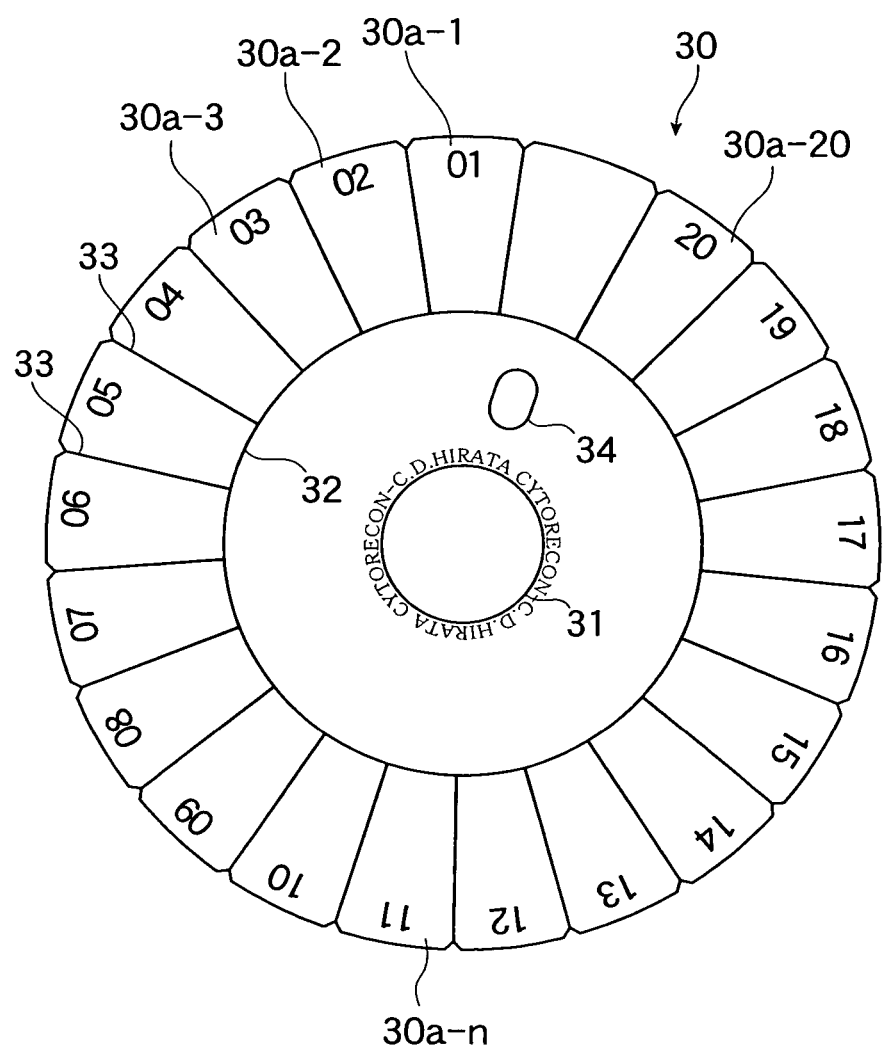
FIG. 5A is a plan view of the protective film.
Figure 5B:
FIG. 5B is a side view of the protective film.

A center hole 31 having a relatively small diameter is formed in a central portion of the protective film 30. The diameter of the center hole 31 is slightly greater than that of the positioning hole 24 of the upper member 16. A relief hole 34 which has an elongated-circle shape as viewed in plane is formed at a position which is slightly biased radially outward. The size of the relief hole 34 is slightly greater than that of the positioning hole 25 of the upper member 16. The protective-film pieces 30*a-n* are marked with Nos. 01 to 20, respectively, which correspond to the liquid-sample accommodation portions 21-*n* (n=1 to 20). Letters indicative of a manufacturer and a product name are marked around the center hole 31. FIG. 5 shows the protective film 30.

By use of the disk 2 and the counting observation apparatus 1 of the first embodiment, counting and observing cells are performed as follows. First, the protective-film pieces 30*a-n* are peeled off from a required number of the liquid-sample accommodation portions 21-*n* (n=1 to 20) of the disk 2 which corresponds to the number of liquid samples to be observed. The liquid samples are injected into the corresponding liquid-sample accommodation portions 21-*n* through the corresponding liquid inlets 22-*n* of the upper member 16. Next, the disk 2 is placed on the rest of the turntable 3. The motor 4 is rotated intermittently so as to intermittently rotate the turntable 3, thereby intermittently rotating the disk 2. During the course of intermittent rotation, the liquid-sample accommodation portions 21-*n* are sequentially brought to and positioned at the observation position of the counting observation apparatus 1. The counting observation apparatus 1 observes the liquid sample contained in the liquid-sample accommodation portion 21-*n* positioned at the observation position, so as to count and observe cells.

In actuality, the counting observation apparatus 1 observes the liquid sample contained in the liquid-sample accommodation portion 21-*n* positioned at the observation position, for counting and observing cells, as follows. The counting observation apparatus 1 does not photograph the entire region of the liquid-sample accommodation portion 21-*n* (in other words, the entire region of the chamber 28-*n*). As shown in FIG. 9, the sample-liquid accommodation portion 21-*n* is divided into a plurality of visual fields 36-*n* (n=1 to 8). The disk 2 is intermittently rotated, by means of the motor 4, at finer pitches, each of which is the spacing between the adjacent visual fields 36-*n* and 36-(n+1). The counting observation apparatus 1 picks up images of the visual fields. From the thus-obtained image data, the number of cells, for example, is counted for each of the visual fields 36-*n*. Cell concentration is determined from an average number of cells among the visual fields 36-*n*. By this procedure, counting and observing cells can be performed with high accuracy and without any bias. The size of each visual field 36-*n* is about 0.5 mm$^2$ (0.7 mm×0.7 mm). All of the eight visual fields 36-*n* are not necessarily subjected to the counting of and observation of cells. One to eight of the visual fields 36-*n* may be selected for counting and observing cells. Also, the total number of the visual fields 36-*n* is not limited to eight.

The disk 2 for storing liquid samples, and the counting observation apparatus 1 for counting and observing cells through an optical microscope by use of the disk 2 according to the first embodiment are configured as described above and thus yield the following effects.

Since the disk 2 for storing liquid samples containing cells is a 3-layer laminate consisting of the upper member 16, the intermediate member 18, and the lower member 17, the disk 2 can be readily fabricated. Since the dimensions of the liquid-sample accommodation portion 21-*n* are determined from the dimensions of each of the chambers 28-*n* of the intermediate member 18 arranged radially for storing the corresponding liquid samples, the dimensions of the liquid-sample accommodation portion 21-*n*; particularly, a depth, can be readily finished at high accuracy. Thus, a highly accurate disk 2 can be readily fabricated at low cost.

Since the disk 2 is fabricated from a disposable material, efficiency in counting and observing cells can be greatly improved. Also, pollution does not arise.

The upper member 16, the intermediate member 18, and the lower member 17 which constitute the disk 2 are formed by blanking. Also, the intermediate member 18 is a film having a uniform thickness and having an adhesive on opposite sides thereof; and the upper member 16, the intermediate member 18, and the lower member 17 are bonded together by means of the adhesive on the opposite sides of the film. Thus, a highly accurate disk 2 can be readily fabricated at low cost.

In the disk 2, a surface of the lower member 17 on a side toward the upper member 16, or a surface of the lower member 17 on a side opposite the upper member 16 is the reflective surface 29. Thus, in the case where the disk 2 is used in the counting observation apparatus 1 for counting and observing cells through an incident-light microscope, the reflective surface 29 can be used to reflect illumination light. Therefore, the configuration of the incident-light microscope becomes simple. In the case where the surface of the rest of the turntable 3 on which the disk 2 is placed is a reflective surface, a similar effect can be yielded.

In the disk 2, the hydrophilic film 20 is vapor-deposited on one or both of mutually opposing surfaces of the upper member 16 and the lower member 17. Thus, a liquid sample introduced through the liquid inlet 22-*n* of the upper member 16 is uniformly distributed within the liquid-sample accommodation portion 21-*n*, whereby the liquid sample can be reliably and stably stored in the liquid-sample accommodation portion 21-*n*.

In the disk 2, the protective film 30 is affixed to an outer surface of the upper member 16 in such a manner that a piece thereof can be peeled off for each of the chambers 28-*n*. Thus, in actual use of the disk 2, the protective-film piece(s) 30*a-n* (n=1 to 20) is peeled off from the required liquid-sample accommodation portion(s) 21-*n* (n=1 to 20), or the required chamber(s) 28-*n* (n=1 to 20). The exposed liquid-sample accommodation portion(s) 21-*n*, or the exposed chamber(s) 28-*n*, are used for counting or observing cells. The remaining liquid-sample accommodation portions 21-*m* (m≠n; m=1 to 20), or the remaining chambers 28-*m* (m≠n; m=1 to 20), are left covered with respective protective-film pieces 30*a-m* (m≠n; m=1 to 20), thereby keeping off dust for later use;

otherwise, adhering dust could cause difficulty in a later process of counting and observing cells.

The counting observation apparatus 1 for counting and observing cells through an optical microscope and by use of the disk 2 can automatically count and observe cells with high reliability, accuracy without any bias, and efficiency by use of the highly accurate, easy-to-fabricate, low-cost disk 2, and can be fabricated at low cost. Further, since the optical microscope can be configured as an incident-light microscope, the counting observation apparatus 1 can be reduced in size.

Second Embodiment

Figure 10:
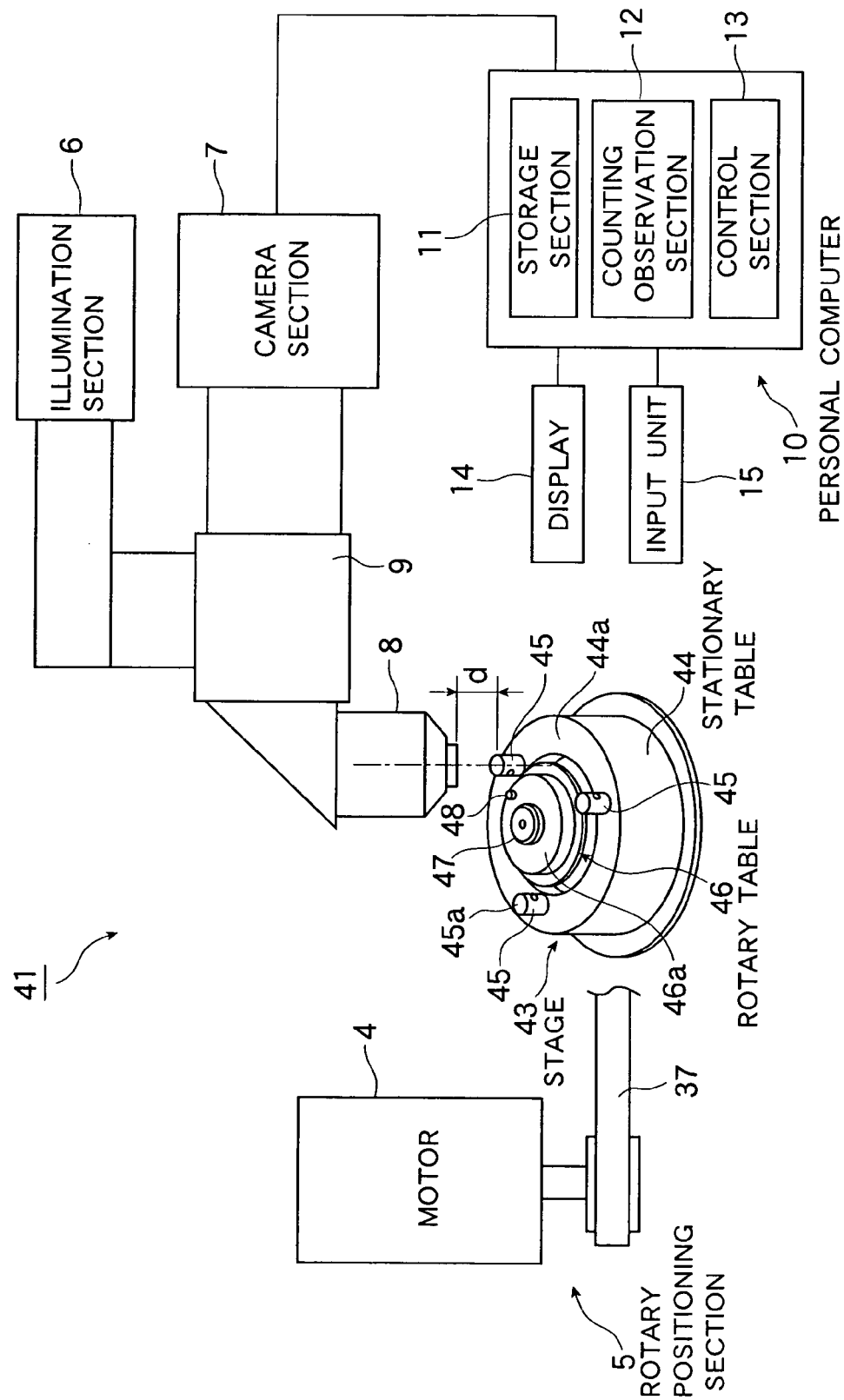
FIG. 10 is a schematic block diagram of a counting observation apparatus for counting and observing cells through an optical microscope by use of a disk for storing liquid samples according to a second embodiment of the present invention.

A second embodiment of the present invention will be described with reference to FIGS. 10 and 11. FIG. 10 is a schematic block diagram of a counting observation apparatus for counting and observing cells through an optical microscope by use of a disk according to the second embodiment. FIG. 11 is a diagram similar to FIG. 10 showing a state in which a disk is placed on a stage of the apparatus. In FIGS. 10 and 11, structural features similar to those of the first embodiment are denoted by like reference numerals.

As shown in FIG. 10, a counting observation apparatus 41 for counting and observing cells through an optical microscope by use of a disk for storing liquid samples according to the second embodiment differs from the counting observation apparatus 1 of the first embodiment only in the structure of a stage 43 on which the disk 2 is placed.

The stage 43 is configured as follows: three support members (pins) 45 for supporting the disk 2 are arranged circumferentially at equal intervals on an upper surface 44a of a stationary table 44. One of the support members 45 is located immediately under the object lens 8 of the image-detecting section (camera section) 7, whereby a constant distance d is maintained therebetween. The number of the support members 45 is not limited to three, but may be more than three. The expression "immediately under the object lens 8" is not used in a strict sense, but is used in a loose sense; in other words, the support member 45 may be located in the vicinity of the position immediately under the object lens 8.

A rotary table 46 is inserted into a cylindrical cavity at a central portion of the stationary table 44 in such a manner as to be concentric with the stationary table 44, and is rotatably supported. Although unillustrated, at a lower portion of the stationary table 44, the rotary table 46 is connected to an output end of the motor 4 via a drive belt 37 and is intermittently rotated by the motor 4.

A short, columnar projection 47 is formed at a central portion of an upper surface 46a of the rotary table 46. A pin-like projection 48 is formed on the upper surface 46a in the vicinity of its circumference and is located a predetermined distance away from the columnar projection 47. The diameter of the columnar projection 47 is substantially equal to that of the positioning hole 24 of the upper member 16. The diameter of the pin-like projection 48 is substantially equal to the width of the positioning hole 25 of the upper member 16.

The disk 2 is placed on the stage 43 in the following manner.

The disk 2 is placed on upper surfaces 45a of the three support members 45, while its positioning hole 24 is fitted to the columnar projection 47 projecting from the upper surface 46a of the rotary table 46 of the stage 43, and its positioning hole 25 is fitted to the pin-like projection 48. At this time, the back surface of the disk 2 is not in contact with the upper surface 46a; i.e., an appropriate clearance is present therebetween. By means of the positioning hole 24 being fitted to the columnar projection 47, centering for rotation of the disk 2 is performed. By means of the positioning hole 25 being fitted to the pin-like projection 48, an initial position for rotation of the disk 2 can be determined.

When the motor 4 is started to start intermittent rotation of the rotary table 46, as a result of the pin-like projection 48 pulling the disk 2 in the circumferential direction, the disk 2 is intermittently rotated about the axis of the columnar projection 47 while sliding on the upper surfaces 45a of the three support members 45. Specifically, first, the disk 2 is rotated by one pitch which is the spacing between the adjacent liquid-sample accommodation portions 21-n and 21-(n+1). Next, the disk 2 is rotated by eight pitches each of which is the spacing between the adjacent visual fields 36-n and 36-(n+1). During the course of this 8-pitch intermittent rotation, the images of the individual visual fields are picked up. This intermittent-rotation pattern is repeated as many as the number of the liquid-sample accommodation portions 21-n (in the second embodiment, 20 times).

Preferably, the upper surface 45a of the support member 45 located immediately under the object lens 8 among the three support members 45 is a reflective surface. This eliminates the need to form either the front or the back surface of the lower member 17 of the disk 2 into the reflective surface 29.

The counting observation apparatus 41 for counting and observing cells through an optical microscope by use of the disk 2 for storing liquid samples according to the second embodiment is configured as described above and thus yield the following effects.

Employment of the three or more support members 45 allows the disk 2 to be supported by the support members 45 and to be rotated while sliding on the supporting surfaces 45a of the support members 45, thereby isolating the disk 2 from operational instability, such as wavy rotation caused by oscillatory movement of the disk-rotating drive system. At an observation position, the disk 2 is supported by the support member 45 located at a position immediately under the object lens 8 or in the vicinity of the position, whereby a constant distance is maintained between the disk 2 and the object lens 8. Thus, automatic counting and observation can be performed with high accuracy.

In the case where the supporting surface 45a of the support member 45 located immediately under the object lens 8 is a reflective surface, cost for vapor deposition for forming the reflective surface can be reduced greatly as compared with the case where the surface of the stage 43 on which the disk 2 is placed is formed into a reflective surface by means of vapor deposition. Accordingly, a low-cost counting observation apparatus for counting and observing cells through an optical microscope can be provided. In the case where, in place of vapor deposition, a mirror member is attached to the support member 45 located immediately under the object lens 8, cost for vapor deposition can be eliminated, and the possibility of quality defect associated with vapor deposition can also be eliminated.

The present invention is not limited to the above-described embodiments. Numerous modifications and variations of the present invention are possible in light of the spirit of the present invention.

What is claimed is:

1. A disk for storing liquid samples containing cells and for use in counting and observing the cells through an optical microscope, the disk comprising:
   an upper member formed of a transparent material and having a plurality of liquid inlets arranged radially and adapted to introduce the corresponding liquid samples therethrough, and a plurality of air vents paired with the corresponding liquid inlets;

an intermediate member having a plurality of chambers extending therethrough, arranged radially and adapted to store the corresponding liquid samples therein, each chamber corresponding to each pair of the liquid inlet and the air vent and communicating with the liquid inlet and with the air vent; and a lower member formed of a transparent material and backing the intermediate member, the lower member presenting a first surface exposed to the liquid samples within the chambers; and wherein the upper member presents a second surface exposed to the liquid samples within the chambers and facing the first surface, the first and second surfaces being located on opposing sides of the intermediate member; and wherein a transparent hydrophilic film forms the second surface of the upper member, or forms the second surface of the upper member and the first surface of the lower member, the hydrophilic film/films causing the liquid samples introduced through the liquid inlets to be uniformly distributed against surface tension within the chambers.

2. A disk according to claim 1, wherein the intermediate member is a film having a uniform thickness and having an adhesive on opposite sides thereof; and the upper member, the intermediate member, and the lower member are bonded together by means of the adhesive on the opposite sides of the film.

3. A disk according to claim 1, wherein the lower member has an upper surface and a lower surface, and wherein said upper surface is the first surface facing the upper member and said lower surface has a reflective film vapor-deposited thereon.

4. A disk according to claim 3, wherein the reflective film is formed of a metal vapor deposition film of aluminum or silver.

5. A counting observation apparatus for counting and observing cells through an optical microscope, comprising:
a disk according to claim 1;
a stage on which the disk is placed;
a rotary positioning section for rotationally positioning the disk;
an illumination section for illuminating the liquid sample with light;
an image-detecting section for picking up an image of the cells and outputting the image in the form of image data;
a storage section for storing the image data;
a counting observation section for counting and observing cells from the image data; and
a control section for controlling the counting observation apparatus;
wherein the storage section, the counting observation section, and the control section are provided in a personal computer as an information processing and manipulating section; and
the chamber is divided into a plurality of visual fields; an image of the cells in each of the visual fields is picked up; the number of the cells is counted from image data associated with the image; and cell concentration is determined from an average number of the cells.

6. A counting observation apparatus for counting and observing cells through an optical microscope according to claim 5, wherein:
the stage comprises three or more support members arranged circumferentially at appropriate intervals for supporting the disk; and
one of the support members is located at a position immediately under an object lens of the image-detecting section or in the vicinity of the position to thereby maintain a constant distance therebetween.

7. A counting observation apparatus for counting and observing cells through an optical microscope, comprising:
a disk according to claim 1;
a stage on which the disk is placed;
a rotary positioning section for rotationally positioning the disk;
an illumination section for illuminating the liquid sample with light;
an image-detecting section for picking up an image of the cells and outputting the image in the form of image data;
a storage section for storing the image data;
a counting observation section for counting and observing cells from the image data; and
a control section for controlling the counting observation apparatus;
wherein the storage section, the counting observation section, and the control section are provided in a personal computer as an information processing and manipulating section;
the chamber is divided into a plurality of visual fields; an image of the cells in each of the visual fields is picked up; the number of the cells is counted from image data associated with the image; and cell concentration is determined from an average number of the cells; and
a surface of the stage on which the disk is placed is a reflective surface.

8. A counting observation apparatus for counting and observing cells through an optical microscope according to claim 7, wherein:
the stage comprises three or more support members arranged circumferentially at appropriate intervals for supporting the disk; and
one of the support members is located at a position immediately under an object lens of the image-detecting section or in the vicinity of the position to thereby maintain a constant distance therebetween.

9. A counting observation apparatus for counting and observing cells through an optical microscope according to claim 8, wherein a disk supporting surface of the support member located at the position immediately under the object lens or in the vicinity of the position is a reflective surface.

10. A disk according to claim 1 wherein the hydrophilic film/films is/are $SiO_2$.

11. A disk according to claim 1 wherein the hydrophilic film/films is/are vapor-deposited on the second surface or on both the first and second surfaces.

* * * * *